United States Patent
Ralovich et al.

(10) Patent No.: US 10,835,321 B2
(45) Date of Patent: Nov. 17, 2020

(54) VIEW ANGLE-INDEPENDENT VISUAL REPRESENTATION OF A CUT PROCEDURE

(71) Applicant: MAKO Surgical Corp., Fort Lauderdale, FL (US)

(72) Inventors: Kristóf Ralovich, Balatonberény (HU); Oliver Kutter, Bad Krozingen-Tunsel (DE); Milán Ikits, Cooper City, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 131 days.

(21) Appl. No.: 16/219,421

(22) Filed: Dec. 13, 2018

(65) Prior Publication Data

US 2019/0183580 A1 Jun. 20, 2019

Related U.S. Application Data

(60) Provisional application No. 62/598,845, filed on Dec. 14, 2017.

(51) Int. Cl.
| | |
|---|---|
| *G06K 9/00* | (2006.01) |
| *A61B 34/10* | (2016.01) |
| *A61B 34/32* | (2016.01) |
| *A61B 17/34* | (2006.01) |
| *A61B 17/16* | (2006.01) |

(Continued)

(52) U.S. Cl.
CPC ............... *A61B 34/10* (2016.02); *A61B 17/16* (2013.01); *A61B 17/34* (2013.01); *A61B 34/20* (2016.02); *A61B 34/30* (2016.02); *A61B 34/32* (2016.02); *A61B 34/70* (2016.02); *G06T 17/10* (2013.01); *G06T 19/00* (2013.01); *G06T 19/20* (2013.01); *G16H 50/50* (2018.01); *A61B 2034/104* (2016.02); *A61B 2034/105* (2016.02); *A61B 2034/108* (2016.02);
(Continued)

(58) Field of Classification Search
None
See application file for complete search history.

(56) References Cited

U.S. PATENT DOCUMENTS

| | | | |
|---|---|---|---|
| 8,958,611 B2 | 2/2015 | Ikits | |
| 2008/0266293 A1* | 10/2008 | Cohen | G06T 13/40 345/424 |

(Continued)

OTHER PUBLICATIONS

International Search Report and Written Opinion for International Application No. PCT/US2018/065478, dated Apr. 2, 2019, 9 pages.

*Primary Examiner* — Wei Wen Yang
(74) *Attorney, Agent, or Firm* — Foley & Lardner LLP (57) ABSTRACT

A computer-implemented method for providing a visual representation of material removal from an object by a cutting tool during a cut procedure is described. The method may comprise tracking consecutive cuts a cut trajectory of the cutting tool during the cut procedure, shape sweeping the consecutive poses of the cutting tool, and, for example, accumulating a union of the cut trajectory in a voxelized constructive solid geometry (CSG) grid to produce an object space representation of the union of the cut trajectory. The computer-implemented method may further comprise performing a CSG operation on object space representation of the union of the cut trajectory and a model of the object, and displaying a result of the CSG operation at a display screen.

20 Claims, 8 Drawing Sheets

(51) Int. Cl.
*G06T 19/20* (2011.01)
*A61B 34/00* (2016.01)
*A61B 34/30* (2016.01)
*A61B 34/20* (2016.01)
*G16H 50/50* (2018.01)
*G06T 17/10* (2006.01)
*G06T 19/00* (2011.01)

(52) U.S. Cl.
CPC ... *A61B 2034/2055* (2016.02); *G06T 2210/41* (2013.01); *G06T 2219/008* (2013.01); *G06T 2219/2021* (2013.01)

(56) References Cited

U.S. PATENT DOCUMENTS

| | | | |
|---|---|---|---|
| 2009/0160855 A1 | 6/2009 | Wu | |
| 2013/0172904 A1 | 7/2013 | Ikits | |
| 2015/0331576 A1* | 11/2015 | Piya | G06F 3/04815 715/850 |
| 2018/0126553 A1* | 5/2018 | Corkum | B25J 9/1692 |
| 2019/0122330 A1* | 4/2019 | Saget | A61B 34/25 |

* cited by examiner

VIEW ANGLE-INDEPENDENT VISUAL REPRESENTATION OF A CUT PROCEDURE

CROSS-REFERENCE TO RELATED APPLICATIONS

This application claims the benefit of and priority to U.S. Application No. 62/598,845, filed on Dec. 14, 2017, which is hereby incorporated by reference herein in its entirety.

BACKGROUND

The present disclosure generally relates to methods and systems for providing a visual representation of a cut procedure and, more specifically, to computer-implemented methods and systems for providing a visual representation of material removal from an object during a cut procedure.

The transformation of a cut procedure into a visual representation is of interest in many applications such as surgery, machining, and milling. For example, there is an interest in developing and improving systems and methods for providing a visual representation of surgical resection procedures as a cutting tool (e.g., burr, saw, reamer, etc.) is penetrating the bone or tissue of a patient. More particularly, providing real time (or perceived real time) updates of the progress of bone or tissue removal at a display screen allows a surgeon or other medical staff to visualize material removal from the bone or tissue as the cutting tool penetrates the bone or tissue. The visual representation allows the surgeon to assess whether the planned region of the bone/tissue has been removed, and whether the cutting tool has penetrated the bone/tissue outside of the planned resection area.

One approach to providing a visual representation of a bone resection procedure is described in U.S. Pat. No. 8,958,611. The method applies a depth peeling procedure to compute the union of consecutive poses of the cutting tool to provide an image space (2D) representation of the cutting tool trajectory. The computed union is then subtracted from the bone model using a constructive solid geometry (CSG) operation to provide an image of the resected bone which is then displayed at a display screen. The results of the calculations are stored as layered depth images (LDIs) at fixed viewing angles of the virtual camera.

While such approaches are effective, the computation of a bone resection procedure may be expensive due to the large number of tool positions that need to be subtracted from the underlying bone model. Due to the nature of the depth peeling procedure, the complexity of the computation (number of rendering passes) increases as the depth complexity of the scene increases. Furthermore, in relying on image space CSG methods, the results of the computation may be invalidated and may require re-computation as soon as the virtual camera is moved or rotated, further adding to the cost and complexity of the computation. In addition, even if the cutting tool travels along a smooth, continuous path during the cutting procedure, the displayed resected bone surface may have visual artifacts such as edgy, ridge-like patterns due to sparse temporal sampling of the tool location. As a result, the displayed resected bone surface may appear somewhat jagged or rough, and may not provide an accurate representation of smooth resected bone surfaces.

Thus, there is a need for improved systems and methods for providing a visual representation of material removal during a cut procedure, such as a bone resection procedure. Specifically, there is a need for systems and methods that reduce the computational cost and complexity of the computation, while also improving the visual quality the displayed image.

SUMMARY

In accordance with one aspect of the present disclosure, a computer-implemented method for providing a visual representation of material removal from an object by a cutting tool during a cut procedure is disclosed. The method may comprise tracking consecutive poses of a cut trajectory of the cutting tool during the cut procedure, shape sweeping the consecutive poses of the cutting tool, and accumulating a union of the cut trajectory in a voxelized constructive solid geometry (CSG) grid to produce an object space representation of the union of the cut trajectory. The method may further comprise performing a CSG operation on the object space representation of the union of the cut trajectory and a model of the object, and displaying a 2D image of a result of the CSG operation at a display screen.

In accordance with another aspect of the present disclosure, a computer-implemented method for providing a visual representation of material removal from an object by a cutting tool during a cut procedure is disclosed. The method may comprise tracking consecutive poses of a cut trajectory of the cutting tool during the cut procedure, and accumulating a union of the cut trajectory in a voxelized constructive solid geometry (CSG) grid to produce an object space representation of the union of the cut trajectory. The method may further comprise performing a CSG operation on the union of the cut trajectory and a model of the object using non-polygonal iso-surface ray marching, and displaying a 2D image of a result of the CSG operation at a display screen.

In accordance with another aspect of the present disclosure, a system for providing a visual representation of material removal from an object by a cutting tool during a cut procedure is disclosed. The system may comprise a robot system having a robotic arm coupled to the cutting tool during the cut procedure, a tracking device configured to track consecutive poses of a cut trajectory of the cutting tool during the cut procedure, and a display screen. The system may further comprise a navigation system in communication with the tracking device and the display screen. The navigation system may have a computer processing unit (CPU) configured to perform shape sweeping of the consecutive poses of the cut trajectory of the cutting tool, accumulate a union of the cut trajectory in a voxelized constructive solid geometry (CSG) grid to produce an object space representation of the union of the cut trajectory, and perform a CSG operation on the union of the cut trajectory and a model of the object using non-polygonal iso-surface ray marching. The CPU may be further configured to display a 2D image of a result of the CSG operation at the display screen, continuously update the object space representation of the union of the cut trajectory in the voxelized CSG grid during the cut procedure, and continuously update the 2D image by repeating the CSG operation on the updated union of the cut trajectory and the model of the object.

It should be understood that the drawings are not necessarily drawn to scale. It is to be further appreciated that the following detailed description is merely exemplary in nature and is not intended to limit the invention or the application and uses thereof. Hence, although the present disclosure is, for convenience of explanation, depicted and described as certain illustrative embodiments, it will be appreciated that it can be implemented in various other types of embodiments and in various other systems and environments.

DETAILED DESCRIPTION

The present disclosure relates to methods and systems for providing a visual representation of material removal from an object by a cutting tool during a cut procedure. For example, the method and system disclosed herein may be used to provide a visual representation of the progress of bone material removal from bone during a surgical bone resection procedure. In other non-limiting examples, the method and system disclosed herein may be used provide a visual representation of material removal in a machining or milling operation. The visual representation may be provided at a display that is updated continuously as the cutting tool penetrates the object so that a user (e.g., a surgeon, etc.) can monitor the progress of material removal in real time (or perceived real time). This allows the user to confirm that only the planned volume of the object has been removed and obtain an instant notification if the cutting tool has penetrates beyond the planned volume. Below is a list of terms and phrases used throughout the present disclosure and their meanings as used herein, many or all of which are apparent to those with ordinary skill in the art.

Constructive Solid Geometry (CSG): a technique for displaying complex geometrical models by combining multiple models using mathematical operations, such as the Boolean set operations of union, intersection, and subtraction.

CSG Operations: the mathematical operations used to combine multiple models to display complex geometrical models, such as the Boolean set operations of union, intersection, and subtraction.

Voxel: volumetric pixel (the volumetric equivalent of a pixel); each of an array of discrete elements into which a representation of a three-dimensional object is divided. Each voxel has a 3D coordinate and holds the color at that coordinate.

Object Space: represented in a three-dimensional voxelized grid.

Rasterization: concept in computer graphics describing how a polygonal geometry is converted into a raster (pixel or voxel) image.

A-Buffer Rasterization: a visible surface detection technique used to identify what is visible in a scene from a specific viewing point of a virtual camera; an extension of the Z-buffer method which adds transparency. A-buffer rasterization creates an A-buffer containing values describing the depth complexity of the scene.

Fragment: one of a plurality of surfaces making up a pixel and contributing to the color of the pixel.

Cut Trajectory: a path that a cutting tool follows during a cut procedure; the volume that the cutting tool has swept through the object up to the current point in time.

Figure 1:
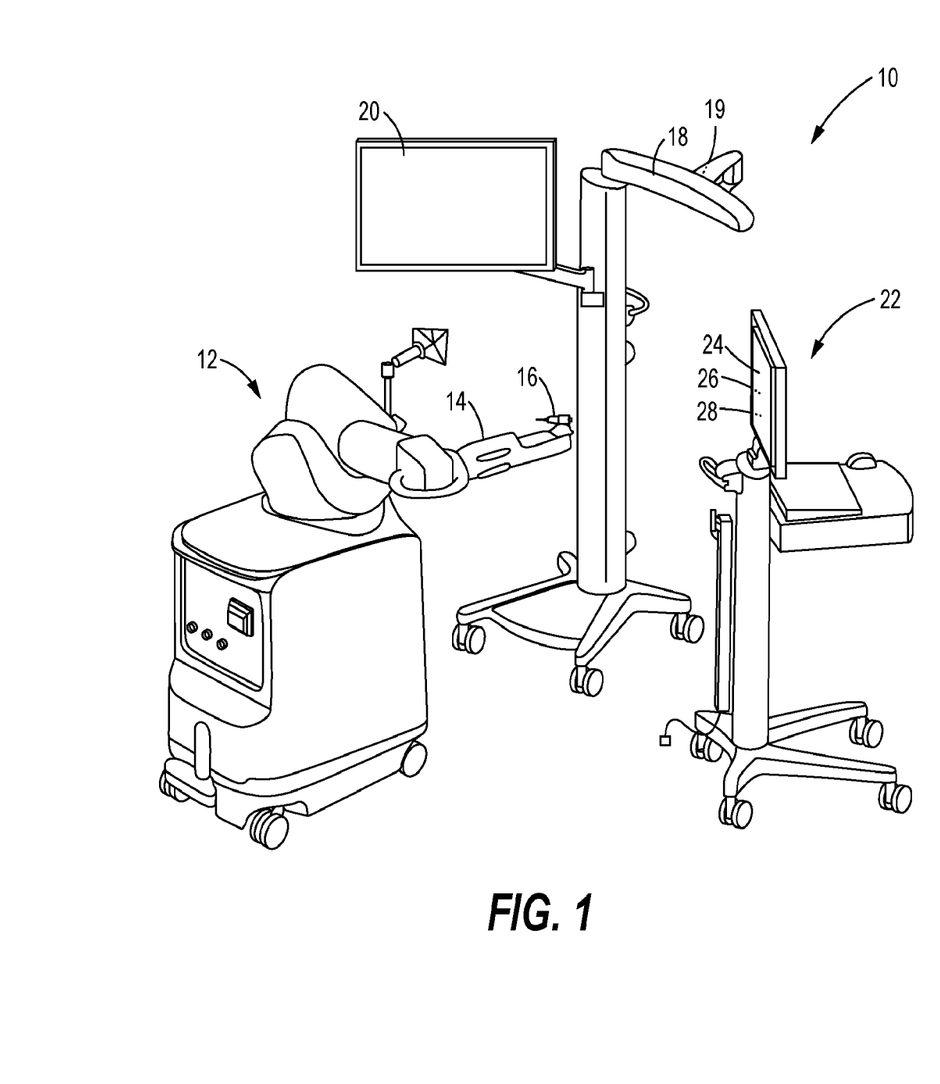
FIG. 1 is a perspective view of a system configured to provide a visual representation of material removal from an object by a cutting tool during a cut procedure, constructed in accordance with the present disclosure.

Referring now to the drawings, and with specific reference to FIG. 1, a system 10 for performing a cut procedure on an object and providing a visual representation of material removal from the object during the cut procedure is shown. As a non-limiting example, the cut procedure may be a surgical tissue or bone resection procedure, such as a hip or knee arthroplasty. Alternatively, the cutting procedure may be a machining or milling procedure. The system 10 may include a robot system 12 having a robotic arm 14 that holds and moves a cutting tool 16 (e.g., a burr, saw, reamer, etc.) during the cut procedure. The system 10 may further include a tracking device 18 having an optical localization system 19 (including an optical localization camera) that tracks the poses (positions/orientations) of the cutting tool 16 and the object to be cut (e.g., bone, etc.) during the cutting procedure. The tracking device 18 may be positioned at a stand or at another location separate from the robot system 12, or it may be positioned at or incorporated into the robot system 12. In addition, the system 10 may include one or more display screens 20 for displaying the visual representation of the cut procedure, and a navigation system 22 in communication with the tracking device 18 and the display screen 20. The navigation system 22 may include a computer 24 having a computer processing unit (CPU) 26 configured to perform one or more algorithms that compute and render the visual representation, and output the visual representation to the display screen 20 as described in further detail below. In some arrangements, the CPU 26 may include a graphics processing unit (GPU) 28 to assist the CPU 26 in performing the rendering calculations.

Figure 2:
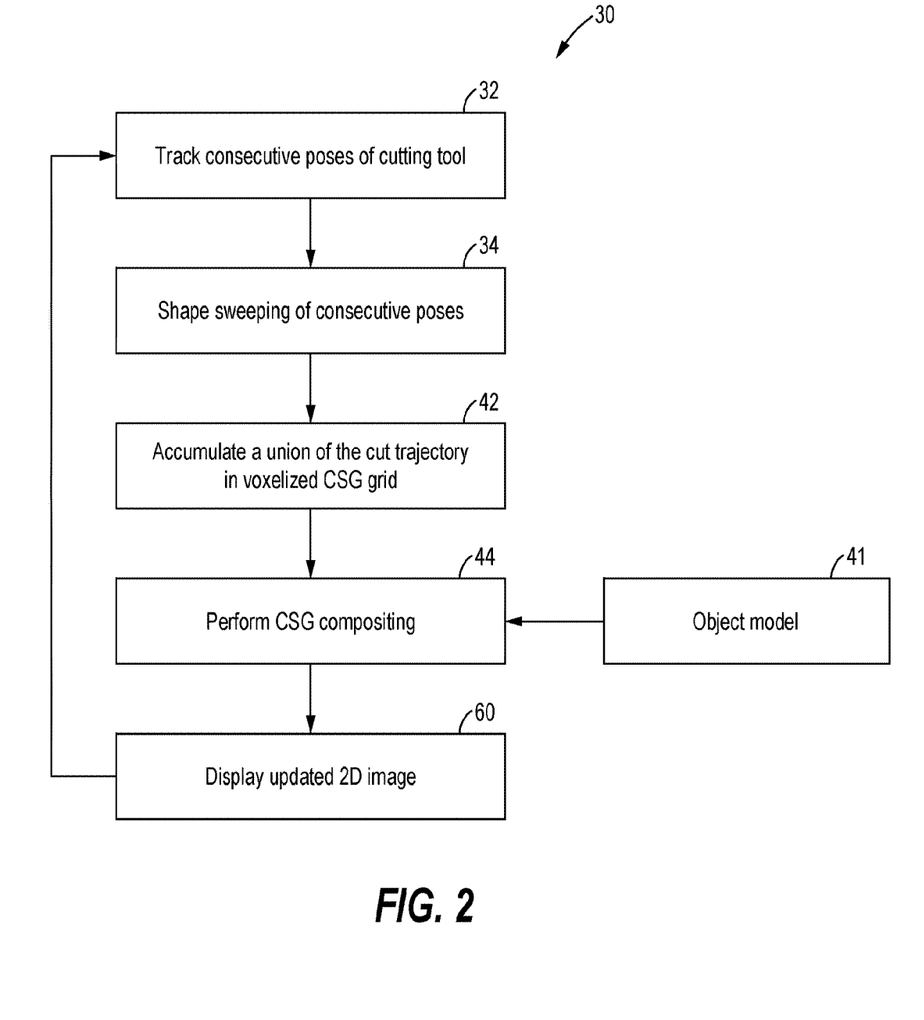
FIG. 2 is a flowchart of a series of steps involved in generating the visual representation of the cut procedure, in accordance with a method of the present disclosure.

Turning now to FIG. 2, a method 30 for generating the visual representation of the cut procedure as performed by the CPU 26 is shown. Further details of the steps of the method 30 are provided below with reference to FIGS. 8-9. At a first block 32, the consecutive poses of the cutting tool 16 as it follows its cutting trajectory during the cut procedure may be tracked based on input from the optical localization system. Each of the consecutive poses represents the discrete position/orientation of the cutting tool 16 at a particular point in time as captured by the optical localization system.

Figure 3:
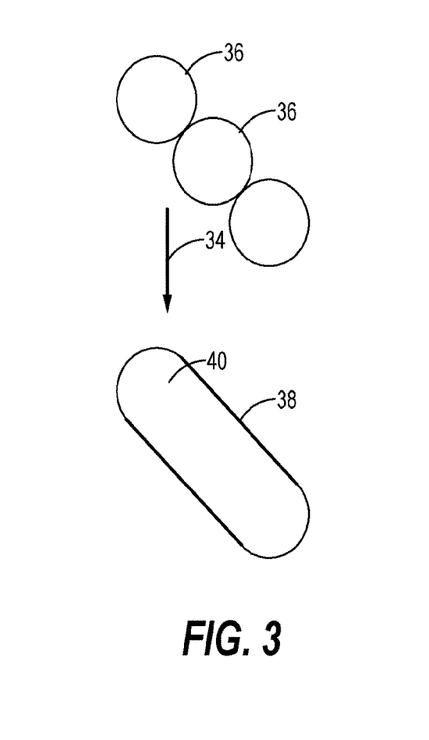
FIG. 3 is a schematic representation of the concept of shape sweeping of consecutive poses of the cutting tool, in accordance with the present disclosure.

Shape sweeping of the consecutive poses of the cutting tool 16 up to the particular point in time may be performed according to a block 34. The concept of the shape sweeping as performed during the block 34 is schematically depicted in FIG. 3. Although the cutting tool 16 may, in actuality, follow a smooth cutting path/trajectory during the cut procedure, the tracked consecutive poses 36 of the cutting tool 16 may be detected as discrete shapes due to sparse temporal sampling of the poses 36 by the tracking device 18. For instance, if the cutting tool 16 is a burr, the tracked consecutive poses 36 may be distinct spherical shapes, as shown in FIG. 3.

To correct for the temporal resolution of the tracking device 18 and provide a smoother visual output that more closely reflects the smooth cutting path followed by the cutting tool 16, shape sweeping 34 may be applied to the consecutive poses 36, as shown. The shape sweeping 34 may enclose the consecutive poses 36 in a smooth surface 38 to provide a smooth representation of a cut trajectory 40 followed by the cutting tool 16. The shape sweeping procedure provides a smoother visual representation of the cut object as explained further below with reference to FIG. 13.

In the example of FIG. 3, the shape sweeping 34 combines the spherical poses 36 into a capsule-like structure having the smooth surface 38. However, it is noted that shape sweeping as disclosed herein may be applied to a variety of cutting tools having different shapes and may be performed on any closed pose geometry such as, but not limited to, burr-ellipsoid/sphere, saw-rectangular cuboid, and reamer/half-sphere shapes. The swept shape may be generated in any suitable fashion, such as via piecewise linear or higher order (e.g., spline) approximation.

Turning back to FIG. 2, a union of the cut trajectory 40 may be accumulated in a three-dimensional voxelized constructive solid geometry (CSG) grid to produce an object space representation of the union of the cut trajectory 40 up to the particular point in time in the cut procedure (block 42). The voxelized CSG grid may be continuously updated with the union of cut trajectory as the cutting procedure progresses. That is, the voxelized CSG grid may be iteratively updated with the current cut trajectory as the position of the tool changes and removes more material from the object during the cut procedure (see below).

According to a next block 44, CSG compositing may be performed. In addition to other steps described further below with reference to FIG. 9, the CSG compositing step may involve performing a CSG operation on the object space representation of the union of the cut trajectory 40 and a three-dimensional model 41 of the object that is being cut. For example, if the object is bone, the three-dimensional model of the bone may be generated by segmenting a computerized tomography (CT) scan of the bone. If the object being cut is of a softer nature, e.g., flesh or a tumor, the three-dimensional model may change lightly between sequential renderings. The CSG operation may be performed using non-polygonal iso-surface ray marching as described further below with reference to FIG. 12.

In the context of a surgical bone resection procedure, for example, the CSG operation performed during the block 44 may be subtraction of the union of the cut trajectory 40 from the bone model to produce a 2D image of the resected bone. However, depending on the procedure that is performed on the object, other types of CSG operations may be performed such as union, intersection, and painting. Further descriptions of some of the types of CSG operations that may be performed during the block 44 are provided below.

Figure 4:
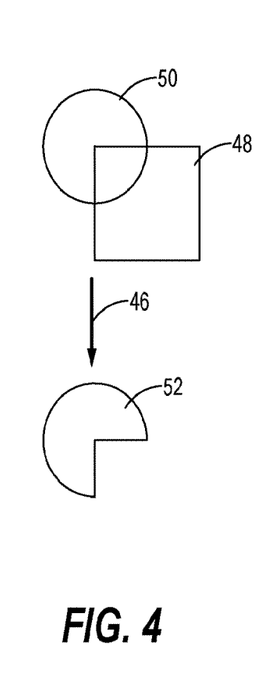
FIG. 4 is a schematic representation of a CSG operation of subtraction, in accordance with the present disclosure.
Figure 5:
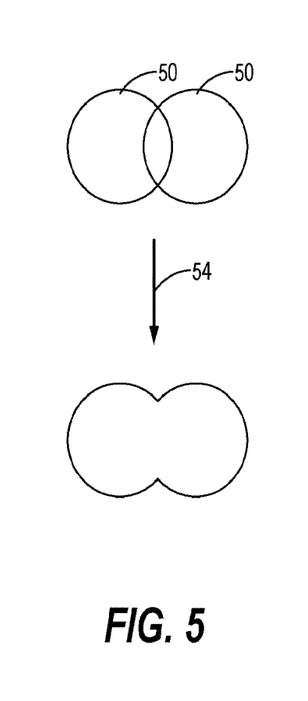
FIG. 5 is a schematic representation of a CSG operation of union, in accordance with the present disclosure.
Figure 6:
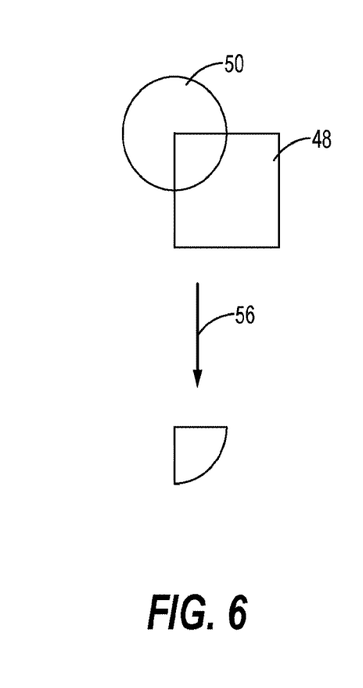
FIG. 6 is a schematic operation of a CSG operation of intersection, in accordance with the present disclosure.

In the CSG operation of subtraction (see FIG. 4), one object is subtracted from a primary object. The operation of subtraction produces a solid having a boundary that is made up of (a) all external points of the primary object that lie outside of the subtracted object, and (b) all external points of the subtracted object that lie inside the primary object. For example, the subtraction 46 of a cube 48 intersecting a quarter of a sphere 50 may be a three-quarter sphere 52 (see FIG. 4). In the CSG operation of union (see FIG. 5), an object is created that combines two or more base objects. Points that are on the boundary of one of the combined objects but are also located internal to other objects are not visible in the combined object. The union 54 of two spheres 50 is schematically depicted in FIG. 5. In the CSG operation of intersection, an object is created from base objects where the boundary is made up of all points that are both external to one object and internal to the other object. For example, FIG. 6 depicts the result of the intersection 56 of a sphere 50 with a cube 48.

Referring again to FIG. 2, upon completion of the block 44, the CPU 26 may output a 2D image of the result of the CSG operation to the display screen 20 (block 60). The 2D image may be continuously updated throughout the cut procedure by repeating the method 30 and continuously displaying the updated 2D image at the display screen 20. The method of FIG. 2 may be repeated with enough frequency so that the 2D image is updated in real time, or at least with enough frequency so that the user perceives the updates as occurring in real time (perceived real time).

Figure 7:
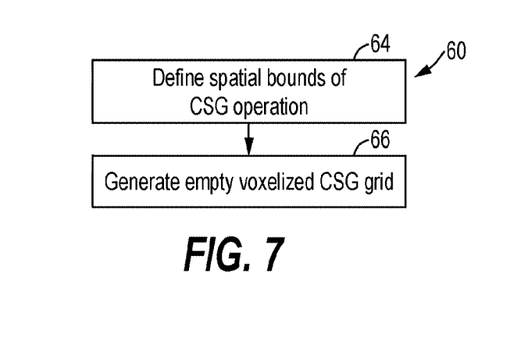
FIG. 7 is a flowchart of steps involved in generating an empty voxelized constructive solid geometry (CSG) grid for accumulation of the union of the cut trajectory, in accordance with a method of the present disclosure.

Prior to accumulating the cut trajectory 40 in the voxelized CSG grid, an empty voxelized CSG grid may be generated according to the method 62 of FIG. 7. Beginning at a block 64, the spatial bounds of the CSG operation may be defined as the intersection of the bounding box (geometric surface) of the object that is cut and the bounding box of the allowed volume of the object that can be removed during the cut procedure. Optionally, a margin may be added to the intersection to allow cuts made outside of the allowed volume to be visualized at the display screen. Once the spatial bounds of the CSG operation has been defined by the block 64, the empty voxelized CSG grid is generated within the defined spatial bounds according to a block 66.

Figure 8:
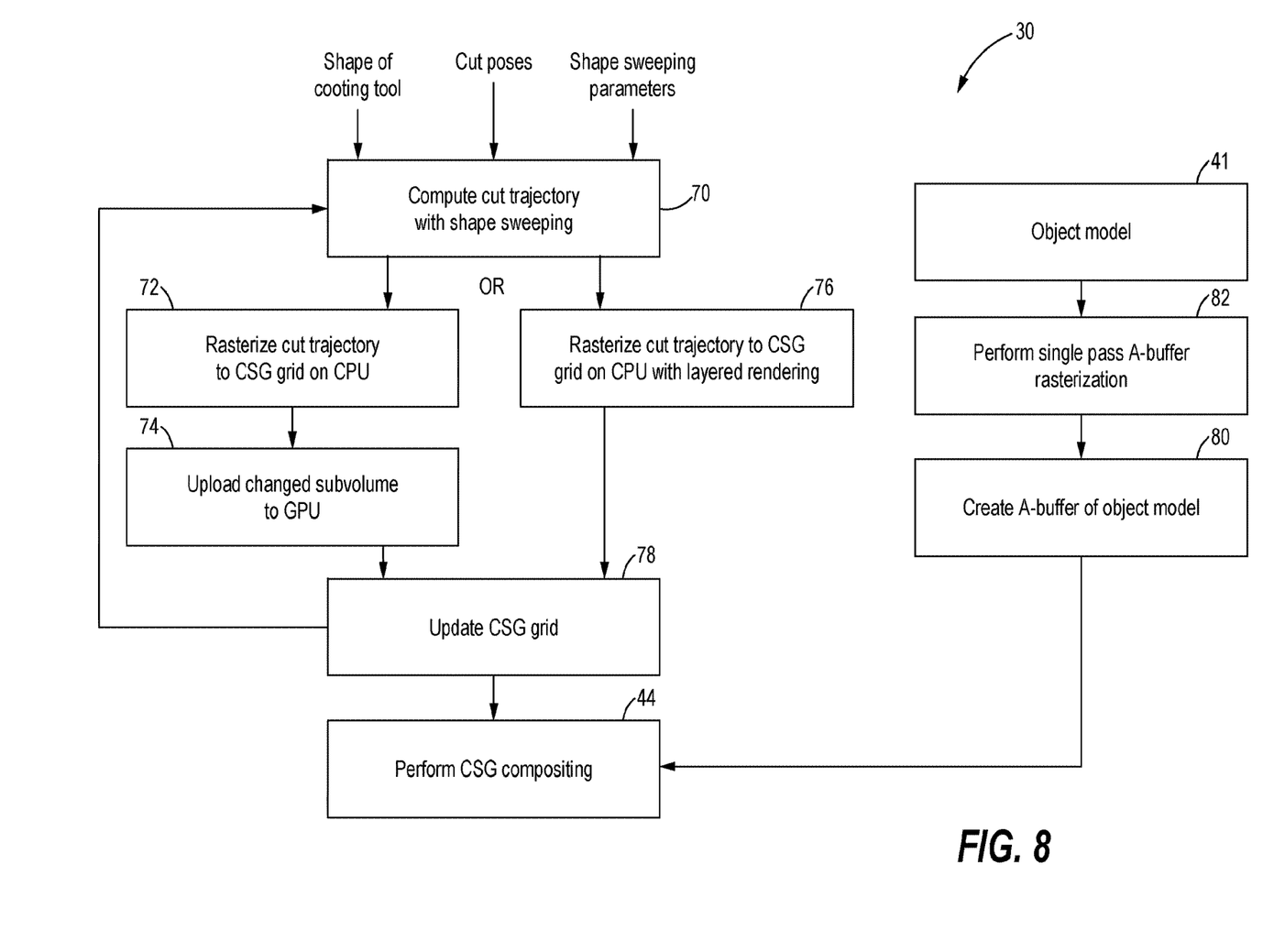
FIG. 8 is a flowchart of a series of steps that may be involved in the method of FIG. 2, in accordance of a method of the present disclosure.

Turning now to FIG. 8, steps that may be involved in the method 30 of FIG. 2 are schematically depicted. At a block 70, the cut trajectory 40 may be computed using shape sweeping 34 taking into account the shape of the cutting tool 16, the tracked consecutive poses 36, as well as the parameters for shape sweeping (also see FIG. 3). The cut trajectory 40 may then be rasterized into the voxelized CSG grid using the GPU 28 or a combination of the CPU 26 and the GPU 28. For instance, the rasterization may be performed on the CPU 26 according to a block 72, and only the sub-volume of the cut trajectory 40 that has changed since the last update may be transferred to the GPU 28 according to a block 74. Alternatively, the rasterization of the cut trajectory 40 may be performed on the GPU 28 according to a block 76. If performed on the GPU 28, the rasterization may be carried out with layered rendering (layer-by-layer rasterization) since the GPU 28 may only be capable of rendering 2D images. As such, one may decide to perform the rasterization by blocks 72 and 74, or by block 76, depending on which strategy is more efficient.

Upon completion of rasterization of the cut trajectory 40, the voxelized CSG grid may be updated with the changed sub-volume of the cut trajectory 40 according to a next block 78. By continuously repeating the blocks 70, 72 and 74 (or 76), and 78 throughout the cut procedure, the union of the cut trajectory 40 may be iteratively updated in the voxelized CSG grid up to the current point in time of the cut procedure.

In addition, an A-buffer of the object model 41 may be created (block 80) by performing single-pass A-buffer rasterization on the object model 41 without a depth test (block 82). Single-pass A-buffer rasterization may reduce the cost of the rasterization as more passes increases the cost of the computation. The A-buffer may be a data structure describing the depth complexity of the object in image space from a viewpoint of a virtual camera. This A-buffer and the updated voxelized CSG grid may be used for the CSG compositing step (block 44) as described in further detail below.

Figure 9:
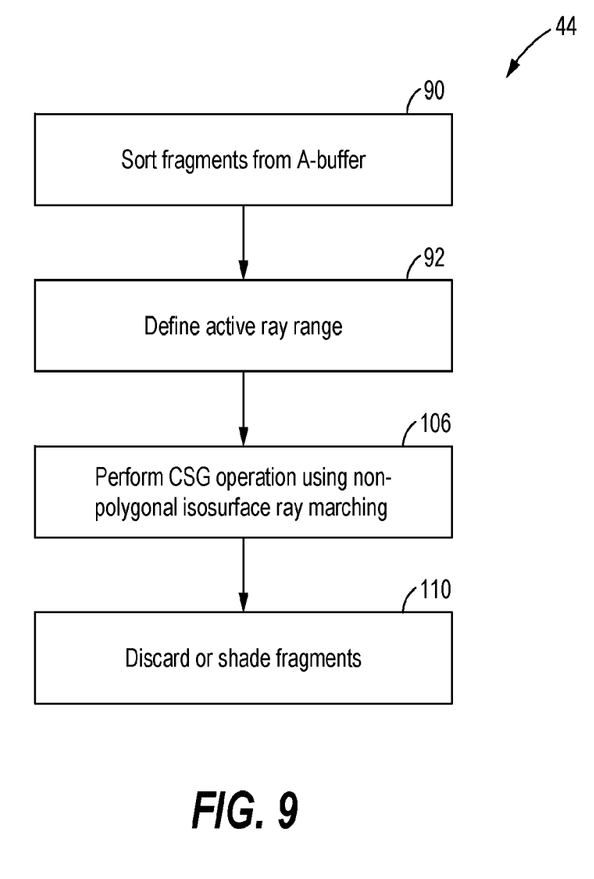
FIG. 9 is a flowchart of a series of steps that may be involved in performing CSG compositing, in accordance with the method of FIG. 2.

Turning now to FIG. 9, steps that may be involved in performing CSG compositing (block 44) are shown. At a first block 90, fragment sorting from the object model A-buffer may be performed. Specifically, the block 90 may involve reading the fragments from the A-buffer and sorting the fragments according to their depths.

Figure 10:
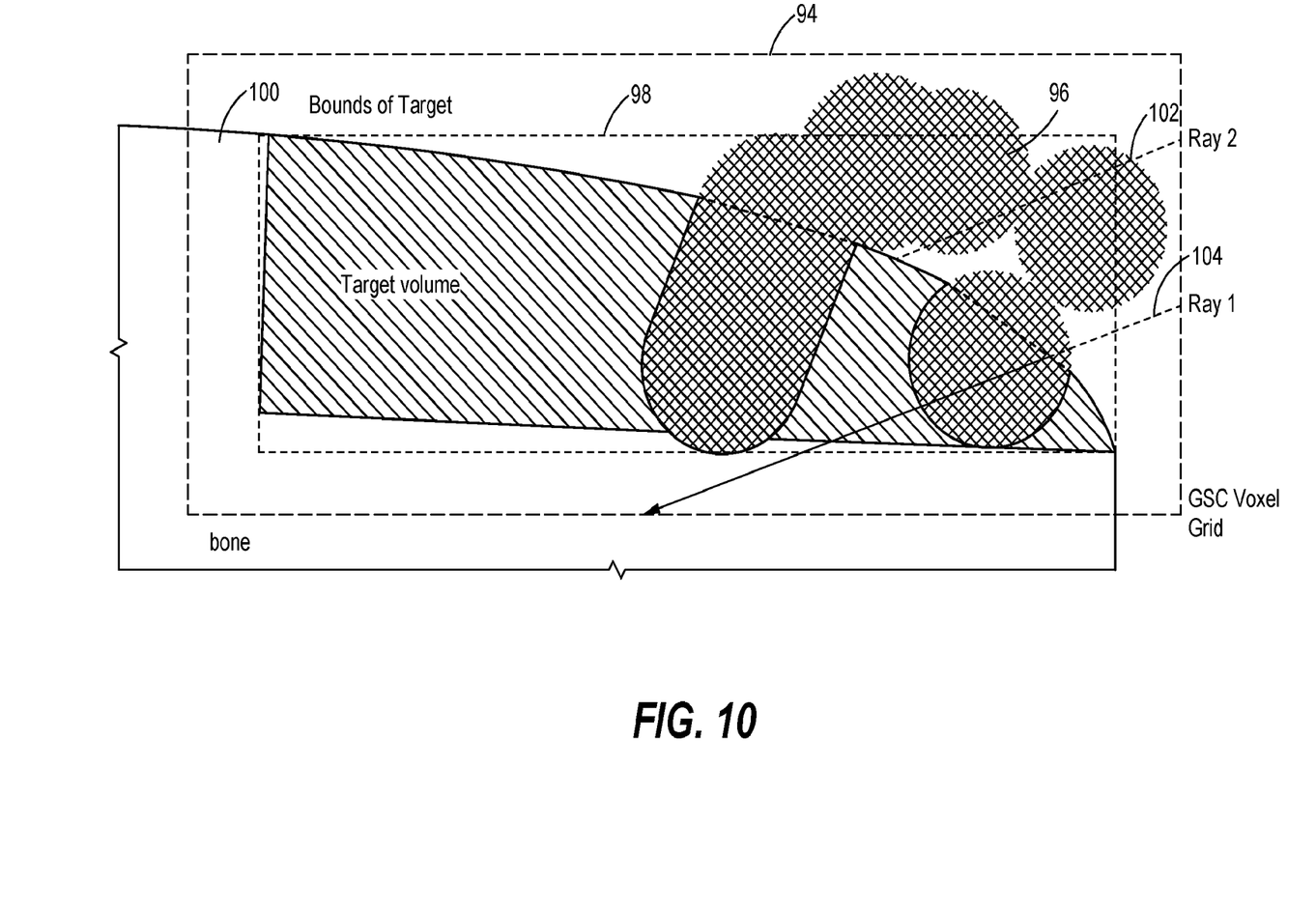
FIG. 10 is a schematic representation of the concept of defining an active ray range for non-polygonal iso-surface ray marching, in accordance with a method of the present disclosure.

At a block 92, the active ray range for non-polygonal iso-surface ray marching may be defined to reduce the active ray range for the ray marching and increase the efficiency of the computation. A schematic illustration of defining the active ray range as performed during the block 92 is shown in FIG. 10. FIG. 10 shows the voxelized CSG grid 94, the union of the cut trajectory 96, and a bounding box 98 of the allowed volume of the object 100 (e.g., bone) that is allowed to be cut during the cut procedure. In non-polygonal iso-surface ray marching, a plurality of rays (e.g., rays 102 and 104) from a particular viewpoint of a virtual camera may be cast or marched through the voxelized CSG grid 94 to iteratively search for intersection points. The intersection points may be used to produce an image space (2D) surface representation of the cut procedure that is displayed at the display screen 20. Each of the rays 102 and 104 may correspond to a pixel in the 2D image that is produced. Defining the active ray range according to the block 92 restricts the search for ray marching and increases the efficiency of the CSG operation. More particularly, according to the block 92, ray marching may be skipped (or "inactive") if the bounding box 98 of the object 100 and the voxelized CSG grid 94 do not overlap along the ray (see dashed sections of exemplary rays 102 and 104 corresponding to the "inactive" ray range). In the "inactive" ray range, no computation is performed. Otherwise, the rays are iterated in the "active" ray range as shown by the solid section of the ray 104. In the "active" ray range, the start of the marching is either the closest surface of the object 100 (from the A-buffer) or where the ray enters the voxelized CSG grid 94, whichever is farther (equation 1). The ray marching is terminated at the furthest intersection of the ray and the object 100 (from the A-buffer), or if CSG grid 94 is exited, whichever happens earlier (equation 2). For example, in FIG. 10, the dashed sections of the exemplary rays 102 and 104 are skipped during marching because they lie outside of the object 100, with ray 102 being terminated as soon as the object 100 is reached since at that point the CSG grid 94 is not set.

$$t_{start} = \max(t_{object\_closest}, t_{grid\_entry}) \quad \text{(equation 1)}$$

$$t_{end} = \min(t_{grid\_exit}, t_{object\_furthest}) \quad \text{(equation 2)}$$

Figure 11:
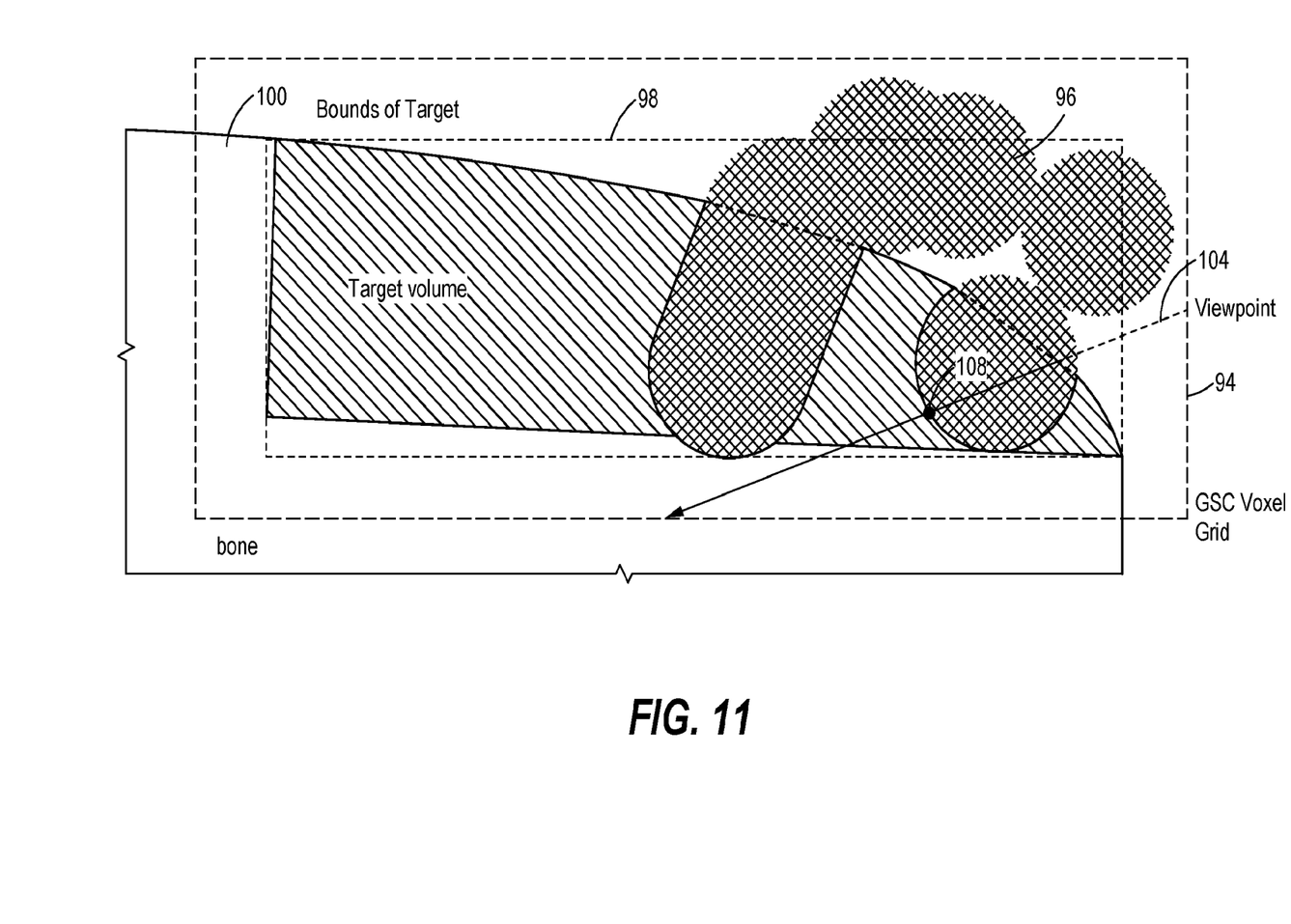
FIG. 11 is a schematic representation of non-polygonal iso-surface ray marching to compute a subtraction of the union of the cut trajectory from the object, in accordance with a method of the present disclosure.

With the active ray range defined as described above, the CSG operation may be performed on the object 100 (from A-buffer) and the union of the cut trajectory 96 using non-polygonal iso-surface ray marching (block 106). It will be appreciated that other CSG operations may be implemented, e.g., surface painting, intersection, etc. FIG. 11 depicts an example of using non-polygonal iso-surface ray marching to display the results of subtracting the union of the cut trajectory 96 from the object 100. For each pixel, a ray 104 is marched through the active ray range (solid portion of the ray 104) from a viewpoint of the virtual camera, and the intersection point 108 is determined as the closest intersection point that is inside the object 100 and outside of the union of the cut trajectory 96. The intersection point 108 represents the cut surface of the object 100, and is used to produce the 2D surface representation that is displayed at the display screen 20.

If the object 100 and the union of the cut trajectory 96 do not overlap along a ray (indicating that the object has not been cut at that location), the object surface is displayed as uncut in the 2D image. Iteratively searching the voxelized CSG grid 94 for intersection points in this manner produces the 2D surface representation of the object as it is cut during the cut procedure. For example, in the context of bone resection, the block 106 may result in a 2D surface representation of the resected bone surface.

Referring again to FIG. 9, the CSG compositing block 44 may further include discarding or shading fragments of the 2D surface representation produced from the CSG operation to refine the 2D image (block 110). In particular, during the block 110, a machining calculation may be applied that determines the shading of each fragment and determines the red, green, and blue color contribution of the fragments at each pixel. In the context of surgical bone resection procedures, regions of bone that are to be resected may be colored in green, and regions where the cutting tool 16 has penetrated beyond the planned region may be colored in red. The block 110 may further involve discarding the fragments that are not visible. The refined 2D image may be displayed at the display screen 20 (block 60, FIG. 2).

In a further embodiment, a display of the total removed material, total material remaining to be removed, or both may be generated for the user's guidance. For example, the display may indicate that 80% of the material to be removed has been removed, and 20% of the material to be removed remains on the object.

Figure 12:
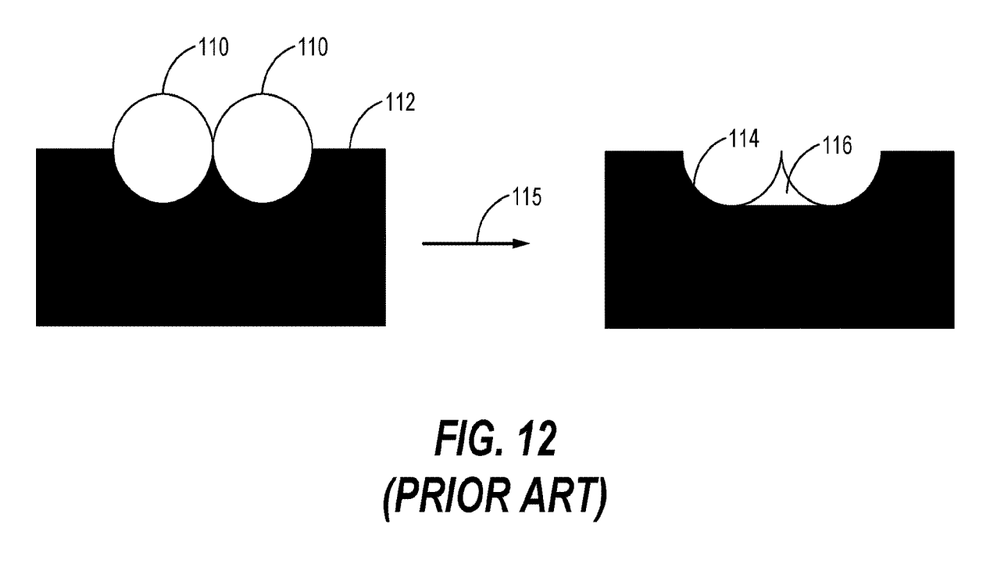
FIG. 12 is schematic representation of subtracting an un-swept cut trajectory from the object, in accordance with the prior art.
Figure 13:
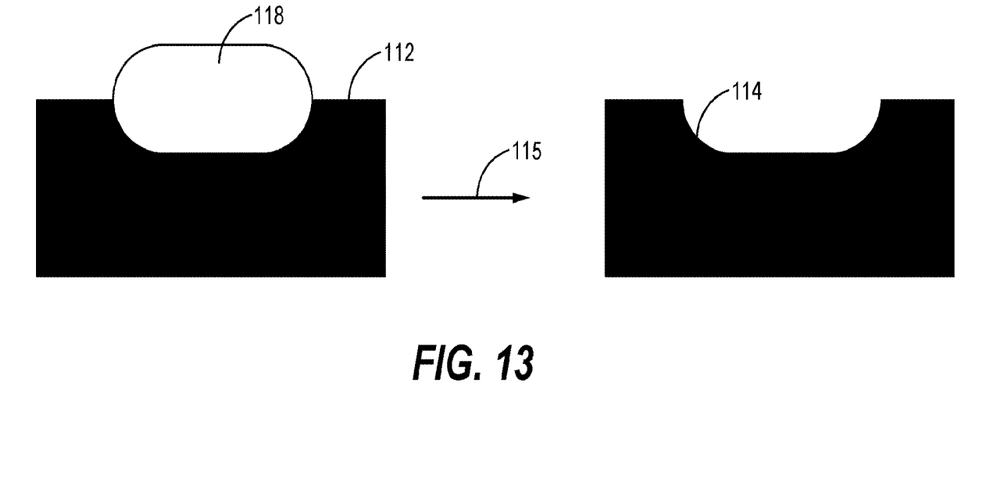
FIG. 13 is a schematic representation of subtracting a swept cut trajectory from the object to produce smooth cut surfaces in the visual representation, in accordance with the present disclosure.

The present application applies shape sweeping 34 to produce a smoother visual representation of the cut procedure. FIG. 12 shows an object surface 114 produced after subtracting un-swept cut poses 110 from an object model 112 in accordance with the prior art. As can be seen, due to the temporal resolution of the tracking method used to track the poses of the cutting tool 16, the poses 110 may be detected as discrete shapes representing the shape of the cutting tool 16. As a result, the displayed object surface 114 after subtraction 115 of the un-swept cut poses 110 may have edgy, wave-like ridges 116 as artifacts of the sparse temporal sampling of the cut poses 110. In contrast, the subtraction of swept cut poses 118 from the object model 112 in accordance with the present disclosure avoids the leftover ridges and produces a smoother visual representation of the cut object surface 114.

INDUSTRIAL APPLICABILITY

In general, it can therefore be seen that the technology disclosed herein may find applicability in a variety of settings such as, but not limited to, surgery and machining. More specifically, the present disclosure may be applicable in various applications that may benefit from real time visualization of the progress of material removal from an object during a manual or automated cut procedure. Although robotic bone resection is given as one example, the technology disclosed herein may also be applicable to manual surgery, such as manual bone resection, to cutting or milling operations, as well as other types of operations.

Current methods used to produce a visual representation of bone resection procedures may be computationally expensive due to the large number of tool positions that need to be subtracted from the bone mod The computational cost of current methods that rely on depth peeling may increase with increasing depth complexity of the scene. Moreover, the results of the computation may be invalidated and require re-computation if the virtual camera is moved or rotated.

By contrast, the method disclosed herein has a constant computational cost with respect to the depth complexity of the scene. The computation of the union of the cut trajectory as disclosed herein happens incrementally at a constant computational cost by rasterizing the model of the cut trajectory to a voxelized CSG grid that (spatially) covers the planned resection volume (with an optional margin). Creating the image-space fragments that describe the voxelized model in a pixel also happens at the constant computational cost of marching rays through the voxelized CSG grid. The resolution of the voxelized CSG grid determines the computational cost, and is fixed beforehand. The voxelized CSG representation also removes the burden of processing overlapping or duplicate positions. Furthermore, high visual quality of resected surfaces is achieved by sub-voxel accurate filtering during non-polygonal iso-surface ray marching. The initial iso-surface intersections are refined in a binary search manner by reducing the marching step size.

As disclosed herein, the voxelized CSG representation may be rasterized on the CPU or on the GPU by layered rendering of the CSG grid into slices, depending on which rasterization strategy is more efficient. If the rasterization happens on the CPU, only the sub-volume of the cut trajectory that has changed since the last update is uploaded to the GPU to further enhance efficiency. This sub-volume is defined by the bounding box of the updated cut pose of the cut trajectory.

The present disclosure also offers another improvement to the quality of the visual representation over existing methods. In current technologies, the consecutive poses of the cutting tool may be too far apart due to sparse temporal sampling of the tool position tracking device, resulting in leftover ridges in the displayed image that may not accurately reflect the smooth cutting path followed by the cutting tool. The present disclosure applies shape sweeping to represent the consecutive poses within a smooth enclosing surface to prevent ridge artifacts from appearing in the visual representation of the cut procedure. Advantageously, this results in visually smoother resected surfaces in the displayed image which may more closely represent the true appearance of the resected object.

What is claimed is:

1. A computer-implemented method for providing a visual representation of material removal from an object by a cutting tool during a cut procedure, comprising:
   tracking consecutive poses of a cut trajectory of the cutting tool during the cut procedure;
   shape sweeping the consecutive poses of the cutting tool;
   accumulating a plurality of the cut trajectories in a voxelized constructive solid geometry (CSG) grid to produce an object space representation associated with the plurality of cut trajectories;
   performing a CSG operation on the object space representation of the plurality of cut trajectories, a target volume, and a model of the object; and
   displaying a 2D image of a result of the CSG operation at a display screen, wherein fragments of the 2D image are shaded based on the CSG operation.

2. The method of claim 1, wherein shape sweeping the consecutive poses of the cutting tool comprises enclosing the consecutive poses in a smooth surface via one of piecewise linear approximation and higher order approximation.

3. The method of claim 2, further comprising continuously updating the 2D image by continuously repeating the method during the cut procedure, and continuously displaying the updated 2D image at the display screen.

4. The method of claim 3, wherein performing the CSG operation comprises non-polygonal iso-surface ray marching.

5. The method of claim 3, wherein performing the CSG operation comprises subtracting the plurality of cut trajectories from the object model using non-polygonal iso-surface ray marching.

6. The method of claim 4, further comprising defining an active ray range for the non-polygonal iso-surface ray marching prior to performing the CSG operation.

7. The method of claim 6, wherein defining the active ray range comprises skipping the ray marching where the voxelized CSG grid and a bounding box of an allowed volume of the object that is allowed to be removed during the cut procedure do not overlap along a ray.

8. The method of claim 1, wherein accumulating the plurality of cut trajectories in the voxelized CSG grid comprises rasterizing the cut trajectory to the voxelized CSG grid using a graphics processing unit (GPU) or a combination of a computer processing unit (CPU) and the GPU.

9. The method of claim 1, wherein the object is a bone, the target volume is a planned resection volume, the cut procedure is a surgical bone resection procedure, and shading of the fragments in the 2D image indicates, in a first color, regions of the bone that are to be resected and indicates, in a second color, regions of the bone where the cutting tool penetrated beyond the planned resection volume.

10. A computer-implemented method for providing a visual representation of material removal from an object by a cutting tool during a cut procedure, comprising:
    tracking consecutive poses of a cut trajectory of the cutting tool during the cut procedure;
    accumulating a plurality of the cut trajectories in a voxelized constructive solid geometry (CSG) grid to produce an object space representation of the plurality of cut trajectories;
    performing a CSG operation on the plurality of cut trajectories, a target volume, and a model of the object using non-polygonal iso-surface ray marching; and
    displaying a 2D image of a result of the CSG operation at a display screen, wherein fragments of the 2D image are shaded based on the CSG operation.

11. The method of claim 10, further comprising defining an active ray range for the non-polygonal iso-surface ray marching prior to performing the non-polygonal iso-surface ray marching, wherein defining the active ray range comprises skipping the ray marching where the voxelized CSG grid and a bounding box of an allowed volume of the object that is allowed to be removed during the cut procedure do not overlap along a ray.

12. The method of claim 10, further comprising shape sweeping the consecutive poses of the cutting tool by enclosing the consecutive poses in a smooth surface.

13. The method of claim 10, further comprising continuously updating the 2D image by continuously repeating the method during the cut procedure, and continuously displaying the updated 2D image at the display screen.

14. The method of claim 10, wherein the CSG operation is a subtraction of a union of the plurality of cut trajectories from the object model.

15. The method of claim 10, further comprising creating an A-buffer from the object model by performing single pass A-buffer rasterization of the object model, wherein the CSG operation is performed using the A-buffer and a union of the plurality of cut trajectories.

16. The method of claim 10, wherein the object is a bone, wherein the cut procedure is a surgical bone resection procedure, and the shading indicates, in a first color, regions of the bone that are to be resected and indicates, in a second color, regions of the bone where the cutting tool penetrated beyond the target volume.

17. A system for providing a visual representation of material removal from an object by a cutting tool during a cut procedure, comprising:
   a robot system having a robotic arm coupled to the cutting tool during the cut procedure;
   a tracking device configured to track consecutive poses of a plurality of cut trajectories of the cutting tool during the cut procedure;
   a display screen;
   a navigation system in communication with the tracking device and the display screen, the navigation system having a computer processor unit (CPU) configured to:
      perform shape sweeping of the consecutive poses of the plurality of cut trajectories the cutting tool;
      accumulate a union of the cut trajectories in a voxelized constructive solid geometry (CSG) grid to produce an object space representation of the union of the cut trajectories,
      perform a CSG operation on the object space representation of the union of the cut trajectories, a planned resection volume, and a model of the object using non-polygonal iso-surface ray marching,
      display a 2D image of a result of the CSG operation at the display screen and shade the 2D image based on CSG operation,
      continuously update the object space representation of the union of the cut trajectories in the voxelized CSG grid during the cut procedure, and
      continuously update the 2D image by repeating the CSG operation on the updated union of the cut trajectories and the model of the object.

18. The system of claim 17, wherein the CPU includes a graphics processing unit (GPU) configured to rasterize the union of the cut trajectory to the voxelized CSG grid.

19. The system of claim 17, wherein the CPU includes a graphics processing unit (GPU), and wherein the CPU is further configured to:
   rasterize the cut trajectory to the voxelized CSG grid; and
   upload a sub-volume of the cut trajectory that has changed since the last update to the GPU, the sub-volume being used to update the object space representation of union of the cut trajectory in the voxelized CSG grid.

20. The system of claim 17, wherein the object is bone, the cut procedure is a surgical bone resection procedure, and the CPU is configured to shade the 2D image based on the CSG operation such that 2D image shows regions of the bone that are to be resected in a first color and shows regions of the bone where the cutting tool penetrated beyond the planned resection volume as a second color.

* * * * *